US007271386B2

(12) United States Patent
Lawrence et al.

(10) Patent No.: US 7,271,386 B2
(45) Date of Patent: Sep. 18, 2007

(54) METHOD FOR DETECTING AND MANAGING NEMATODE POPULATION

(75) Inventors: Gary W. Lawrence, Starkville, MS (US); Roger King, Starkville, MS (US); Amber T. Kelley, Birmingham, AL (US); John Vickery, Centerville, OH (US)

(73) Assignee: Mississippi State University, Mississippi State, MS (US)

( * ) Notice: Subject to any disclaimer, the term of this patent is extended or adjusted under 35 U.S.C. 154(b) by 43 days.

(21) Appl. No.: 11/156,675

(22) Filed: Jun. 21, 2005

(65) Prior Publication Data

US 2006/0006335 A1    Jan. 12, 2006

Related U.S. Application Data

(60) Provisional application No. 60/580,911, filed on Jun. 21, 2004.

(51) Int. Cl.
*G01J 5/02* (2006.01)

(52) U.S. Cl. ............................................. 250/339.11

(58) Field of Classification Search ............ 250/339.11
See application file for complete search history.

(56) References Cited

U.S. PATENT DOCUMENTS

| 5,023,173 | A | * | 6/1991 | Horwitz et al. ............... 435/29 |
| 5,213,830 | A | * | 5/1993 | Haagensen et al. ......... 426/237 |
| 6,366,681 | B1 | * | 4/2002 | Hutchins .................... 382/110 |
| 6,651,914 | B1 | * | 11/2003 | Langenecker ............ 241/24.23 |

OTHER PUBLICATIONS

Gausman, et al., "Effect of *Rotylenchulus reinformis* on Reflectance of Cotton Plant Leaves", Journal of Nematology, vol. 7, No. 4, pp. 368-373, 1975.
Kelley, "Estimation of Population Thresholds of Plant-Parasitic Nematodes on Cotton Using Hyperspectral Remotely Sensed Data", A Thesis Submitted to the Faculty of Mississippi State University, Mississippi State, Mississippi, entire document, 2003.

* cited by examiner

*Primary Examiner*—David Porta
*Assistant Examiner*—Marcus Taningco
(74) *Attorney, Agent, or Firm*—DLA Piper US LLP

(57) ABSTRACT

The present invention is directed to methods and apparatus for pest management using remote sensing technology. One aspect of the present invention relates to a method for detecting plant-parasitic nematodes using hyperspectral reflectance data. Another aspect of the present invention relates to a device for determining the population of reniform nematode in a target. The further aspect of the present invention relates to a method for managing nematode population with variable rate applications of nematicides.

20 Claims, 3 Drawing Sheets

FIG. 1

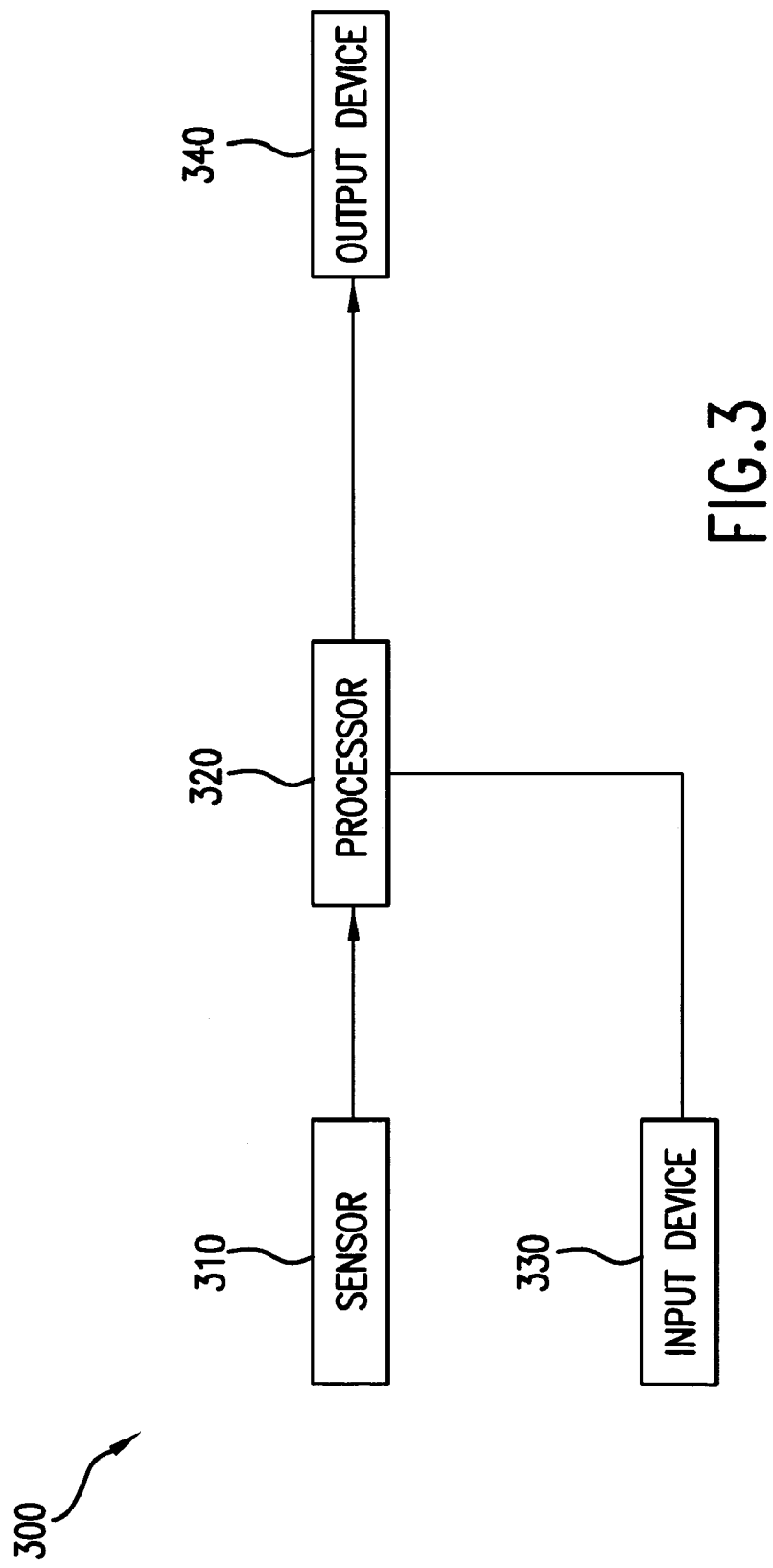

METHOD FOR DETECTING AND MANAGING NEMATODE POPULATION

This application claims priority from U.S. Provisional Application Ser. No. 60/580,911 filed Jun. 21, 2004. The entirety of that provisional application is incorporated herein by reference.

The present invention was made with Government support under NAG13-03012 awarded by the National Aeronautics and Space Administration. The Government may have certain rights in the invention.

FIELD OF THE INVENTION

The present invention generally relates to the field of plant-parasites. More particularly, the present invention relates to methods and apparatus for detecting plant-parasitic nematodes using remote sensing technology. The methods and apparatus are particularly useful for pest management.

BACKGROUND OF THE INVENTION

Cotton is one of the important cash crops in not only Mississippi, but also the entire United States. Pests, such as plant-parasitic nematodes are a serious economic threat to cotton production. The *Rotylenchulus reniformis* (reniform nematode) is one of the most prevalent cotton parasites in the southeastern United States. The reniform nematode may cause a cotton crop yield loss as high as 40–60%.

The reniform nematode produces visible damage, such as reduced root system, reduced boll size, reduced plant size, a yellowish cast of color on the plant, and sometimes a purple hue to the leaf margins. Nematicides are the most frequently utilized means of nematode management. Nonetheless, when visible effects can be observed by the naked eye, the cotton crop has already lost most of its potential economic return. In order to decrease that loss, nematode detection needs to be made early in the infection, and the correct population estimate is required to determine the proper treatment of the infection.

Currently, to gage the reniform nematode population, soil samples must be collected from the cotton fields. The samples must be placed in a similar water proof bag and kept cool. Each zip-lock bag must be specifically labeled and sent to a testing laboratory as soon as possible. The laboratory performs the test to determine nematode population in the samples. The entire process is costly and time consuming, taking two weeks to several months. When the producer receives the results weeks later, they may have lost their window of an opportunity to effectively implement a nematode management program, costing the producers even more in economic returns. Accordingly, there is a need for rapid detection of reniform nematode infection in cotton plants and effective management of the reniform nematode population.

SUMMARY OF THE INVENTION

One aspect of the present invention relates to a method for detecting *Rotylenchulus reniformis* (reniform nematode) in a target. The method comprises the steps of: collecting reflectance data from the target at wavelengths indicative of nematode infestation; and detecting the presence of nematodes based on intensities of the reflectance data. In one embodiment, the method further comprises the step of analyzing the intensities of the selected bandwidths to determine nematode population in the target.

Another aspect of the present invention relates to a device for determining the population of reniform nematode in a target. The device comprises: (a) a sensor for collecting reflectance data from the target; (b) a data processor for analyzing intensities of the reflectance data at wavelengths which are associated with the presence of nematodes to determine whether nematodes are present in or at the target.

Yet another aspect of the present invention relates to a method for controlling reniform nematode population in a cotton field. The method comprises the steps of determining spatial distribution of nematode in a cotton field, and applying nematicide in amounts proportional to nematode density.

BRIEF DESCRIPTION OF FIGURES

Figure 1:
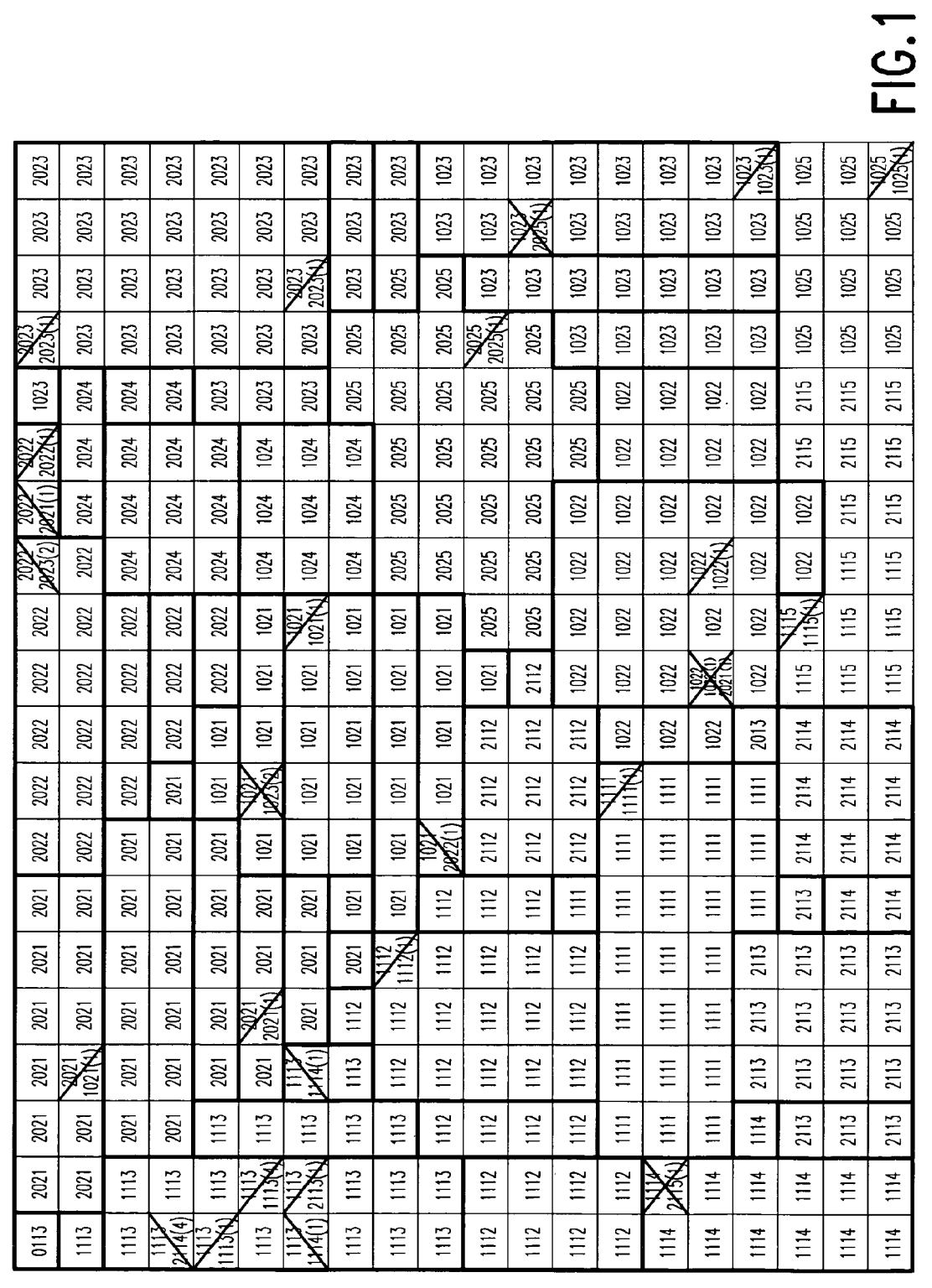

FIG. 1 is a self-organized map (SOM). Color groups indicate hyperspectral data points with similar characteristics.

FIG. 3 is a block diagram of a system for detecting and classifying nematode infestation according to an embodiment of the invention.

DETAILED DESCRIPTION OF THE INVENTION

Figure 2:
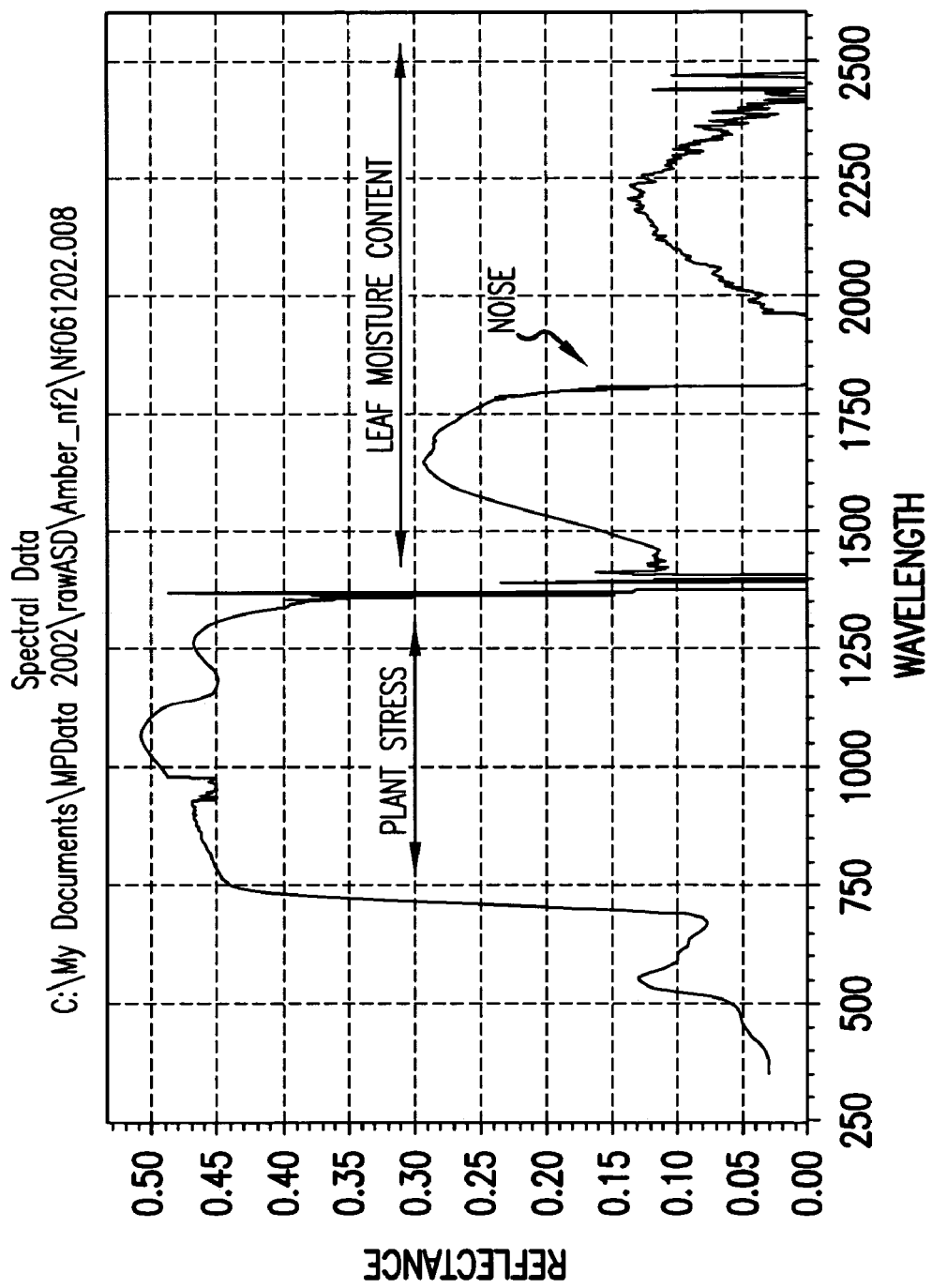
FIG. 2 is a representative curve of the intensity as a function of the frequency from a hyperspectral reading.

The following detailed description is presented to enable any person skilled in the art to make and use the invention. For purposes of explanation, specific nomenclature is set forth to provide a thorough understanding of the present invention. However, it will be apparent to one skilled in the art that these specific details are not required to practice the invention. Descriptions of specific applications are provided only as representative examples. Various modifications to the preferred embodiments will be readily apparent to one skilled in the art, and the general principles defined herein may be applied to other embodiments and applications without departing from the scope of the invention. The present invention is not intended to be limited to the embodiments shown, but is to be accorded the widest possible scope consistent with the principles and features disclosed herein.

The present invention is directed to methods and devices for the detection and management of reniform nematode population in a cotton production system. One aspect of the present invention relates to a method for the detection and population estimation of reniform nematode on cotton using hyperspectral reflectance measured by a remote sensing device.

Remote sensing is the characterization of an object without coming into actual physical contact with that object. One embodiment of a remote sensing device is an advanced imaging system such as a camera. The advanced imaging system uses an energy source, such as a camera flash or sunlight, to provide enough electromagnetic energy to be reflected or emitted so that the reflected/emitted energy can be captured in a visual image form. While regular cameras only allow visualization of a small portion of the electromagnetic spectrum (400–700 nm) that is visible to the naked eye, the advanced imaging system is capable of detection of other components of the electromagnetic spectrum include, not but limited to, gamma rays, x-rays, ultraviolet rays, near-infrared rays (NIR), infrared rays, and other areas of the electromagnetic spectrum. Accordingly, an advanced imaging system, such as a hand-held hyperspectroradiometer, can provide users with spectral information about objects in areas of the electromagnetic spectrum that cannot be observed by the naked eye.

In one embodiment, the advanced imaging system is capable of collecting hyperspectral reflectance data at wavelengths of less than 400 nm in addition to wavelengths from the visible spectrum. In another embodiment, the advanced imaging system is capable of collecting hyperspectral reflectance data at wavelengths of greater than 700 nm in addition to wavelengths from the visible spectrum.

In a preferred embodiment, the advanced imaging system is capable of collecting hyperspectral reflectance data in the NIR plateau of 700–1300 nm. It is known to one skilled in the art that a plant exhibiting a high reflectance in the NIR plateau indicates good plant health.

In another preferred embodiment, the advanced imaging system is capable of collecting hyperspectral reflectance data of the short-wave infrared rays (SWIR), which ranges from 1300–2500 nm. The lower the reflectance of SWIR, the higher the water content in the plant leaf, and vice versa. Therefore, SWIR can be used to monitor plant transpiration. Moreover, Gausman et al. have shown that nematode stressed leaves have a lower reflectance value than non-stressed leaves. Accordingly, reflectance values of cotton leaves can be used to distinguish between nematode infested cotton plants and non-nematode infested cotton plants. [Gausman et al., *J. of Nematology* 7(4):368–373, (1975)].

In another embodiment, remote sensing takes place from an airborne platform or an orbiting satellite. These forms of remote sensing, however, are subject to many factors, such as atmospheric conditions and the sun angle, which may affect the sensing data. In a preferred embodiment, the advanced imaging system used for remote sensing is a hand-held hyperspectroradiometer. Hand-held hyperspectroradiometers have several advantages over other methods of remote sensing. These advantages include the use of white light to account for atmospheric conditions and the sun angle and the minimization of cost. In addition, hand-held hyperspectroradiometers can be used concurrently with a global positioning system (GPS) to accurately relate a specific location to hyperspectral measurements. The hyperspectral reflectance readings can be taken from the cotton plant canopy, the soil, the cotton plant canopy and the soil simultaneously, or a single cotton plant leaf.

Reflectance data can be either hyperspectral or multispectral. These two terms refer to the amount of spectral information collected by the remote sensory device. Multispectral refers to data acquired of wavelengths in less than 300 wave bands or channels. These bands are not contiguous, and thus, many wavelengths are not sampled. Multispectral data is easier to analyze than hyperspectral data because of the lower bulk of information. Multispectral data is typically used in target discrimination, whereas hyperspectral data is typically used in target identification because of the amount of available data and detail. Hyperspectral data is composed of three dimensions: sample number, band (or channel) number, and amplitude. Hyperspectral data is important in situations where the spectral band or bands of interest are unknown because of the immense amount of information provided by the data. The reflectance data is transferred to a mathematical and computational engine, where the data is read, condensed, and analyzed.

In one embodiment, the reflectance data is hyperspectral. The hyperspectral reflectance data is fed from the advanced imaging system into a computer with a program that takes the hyperspectral reflectance data and plots a curve of the intensity of each hyperspectral bandwidth (FIG. 1). The hyperspectral reflectance curves are then entered into a mathematical and computational engine that converts those curves into numerical data, analyzes the data, and identifies the hyperspectral channels that best compare to the frequencies associated with the presence of nematode populations. In one embodiment, the program that plots hyperspectral reflectance curves is ViewSpecProbe which is included with the commercially available FIELDSPEC® line of spectroradiometers from Analytical Spectral Devices, Inc. (www.asdi.com/products-FSP.asp). In another embodiment, the mathematical and computational engine is a MATLAB based hyperspectral tool kit (MHTK). In yet another embodiment, the MHTK uses a spectral analysis program somtoolbox2 to identify the hyperspectral channels that best compare to the frequencies associated with the presence of nematode populations.

The number of wavebands/channels chosen from each hyperspectral reading is not set to a specific number, but is normally in the range of 2–128, preferably in the range of 4–64, and more preferably in the range of 8–32. In one embodiment, 16 channels were chosen from each hyperspectral reading.

The MHTK performs hyperspectral analysis by comparing the hyperspectral bandwidths from the hyperspectral reading with data already built into an artificial neural network (ANN). The built-in data are hyperspectral bandwidths associated with the presence of nematode populations that have been taken from a control group of known nematode populations. The hyperspectral bandwidths chosen by the spectral analysis program are analyzed, compared with the built-in data from the control group, and assigned a value corresponding to a given nematode population.

In one embodiment, five values are assigned to five ranges of nematode populations. For example, a value of 1 means a nematode population of 0 to 500 per 500 cubic centimeters ($cm^3$) of soil; a value of 2 means a nematode population of 500 to 1000 per 500 $cm^3$ of soil; a value of 3 means a nematode population of 1000 to 5000 per 500 $cm^3$ of soil; a value of 4 means a nematode population of greater than 5000 per 500 $cm^3$ of soil; and a value of 5 means no nematode population per 500 $cm^3$ of soil.

In a preferred embodiment, the MHTK has three main components: the graphical user interface (GUI) routines, the batch routines, and the functional routines. The GUI allows a user to enter data on each hyperspectral reading. The data may include a number for the plot area, the light source, and the spectral target. For example, under title of light source, the user may enter 0 for a hyperspectral reading taken under natural light and 1 for a hyperspectral reading taken under artificial light. Similarly, under the title of spectral target, the user may enter 1 for a hyperspectral reading taken from a single leaf and 2 for a hyperspectral reading taken from the canopy. Each plot area is numbered, and the corresponding number is entered for each hyperspectral reading. The GUI also allows the user to manage data, filter unneeded bands, and request the performance of desired analysis. The user may also use data batches or batch routines to analyze up to nine data sets at once, allowing for multi-temporal hyperspectral data flow. The functional routines are the portion of the MHTK that actually performs the analysis functions as directed by the GUI routines or batch routines. The plot area may be the entire field, a section of a field, or such other area as required. Several plots may be selected within a field or area to get representative hyperspectral readings.

In an embodiment, the MHTK works in conjunction with a self-organized map (SOM) to display the hyperspectral reflectance data. In a preferred embodiment, the SOM plots the hyperspectral reflectance data into a two-dimensional (2D) format and each hyperspectral reading is represented by a square on the 2D plot. In a most preferred embodiment, each square has a four digit grid number displayed in the box (FIG. 1). The first three digits of the grid number are represented by the information entered into the GUI of the MHTK, with the first digit representing the plot number, the second digit representing the type of light source, and the third digit representing the spectral target from which the hyperspectral reading was taken. The fourth digit represents the nematode population range as determined by the MHTK's analyzing and comparing of the hyperspectral reflectance data. Squares of similar data are grouped together using the Euclidian distance formula on the SOM's 2D plot and color-coded for easy visualization.

In one embodiment, hyperspectral date is collected from control cotton plants with known population levels of reniform nematodes. The cotton plants are infested with reniform nematode populations of 0, 2500, 5000, 7500, and 10000 per 500 $cm^3$ of soil. Reflectance readings are made by the hand-held hyperspectroradiometer biweekly of the plant canopy alone, the plant canopy and soil together, and the soil alone. Each cotton plant contains the Bt gene for insect resistance. In another embodiment, the same method is used, except the cotton plants are each sprayed with an insecticide spray. Data collected from the control cotton plants is built into the ANN for use in comparing hyperspectral reflectance readings. Briefly, hyperspectral reflectance data of cotton plants with unknown nematode populations are measured using the steps described above. The results are then compared with the results of the control group for final estimations. A more detailed description can be found in "Estimation of Population Thresholds of Plant-Parasitic Nematodes on Cotton Using Hyperspectral Remotely Sensed Data" Amber Thomas Kelley, Master's Thesis 2003, available from the library at Mississippi State University, which is herein incorporated by reference.

Another aspect of the present invention relates to a device for detecting and/or determining the population of reniform nematode in a target. The device comprises (a) a sensing means for collecting hyperspectral reflectance data from the target, (b) a computing means for plotting the intensity of the hyperspectral reflectance data; converting the plotted hyperspectral reflectance data into numerical form; identifying bandwidths that are associated with the presence of nematode populations; and analyzing the identified bandwidths to determine nematode population in the target; and (c) a means for displaying the hyperspectral reflectance data.

As discussed above, the sensing means can be an advanced image system capable of providing spectral information from the electromagnetic spectrum that cannot be observed by the naked eye. In a preferred embodiment, the sensing means is a hand-held hyperspectroradiometer. In another preferred embodiment, the computing means is a MATLAB based hyperspectral tool kit.

Yet another aspect of the present invention relates to a method for controlling reniform nematode population in a cotton field. The method uses variable rate nematicide applications for the management of the reniform nematode.

Plant-parasitic nematodes have a spatial distribution that is in a scattered pattern across a field. Areas also exist where there are no nematodes. Other areas may seem uniformly infested with the nematode but the population numbers vary. This has been shown to be an ideal situation for site-specific nematicide applications using variable rate technology. Accordingly, the method of the present invention comprises the steps of determining spatial distribution of nematode in a cotton field; and applying nematicide in amounts proportional to nematode distribution with variable rate applicator.

In a preferred embodiment, the spatial distribution of nematode is determined using the method described above. In another preferred embodiment, the variable rate applicator is capable of distributing nematicide in both liquid and granule forms.

The present invention is further illustrated by the following examples which should not be construed as limiting. The contents of all references, patents and published patent applications cited throughout this application, as well as the Figures and Tables are incorporated herein by reference.

EXAMPLE 1

Microplot Study for the 2001 Growing Season

Microplots are fiberglass cylinders, which are 2' long×2' in diameter and inserted 18" into the ground. Microplots are similar to large isolated pots in which nematode numbers can be critically controlled while subjecting the cotton plants to natural conditions.

Hyperspectral ground data, chlorophyll data, plant growth development data, nutrient data, temperature and humidity data were collected in the microplot study over eight separate dates during the 2001 growing season. Biweekly collection dates for the microplots were: 11 June, 19 June, 25 June, 10 July, 27 July, 06 August, 20 August, and 11 September. Microplot imagery was collected, but is not useful due to spatial resolution.

Canopy with soil, single leaf, and plant canopy spectral measurements and corresponding reniform nematode population levels were analyzed using the MHTK with SOMs. Water bands and bands containing electronic noise were removed prior to SOM analysis. Two batches of SOMs were run for each target. The first batch concentrated on wavelengths 451–949 (visible and NIR regions of the EMS). The second batch ran with not only wavelengths 451–949 but also 1001–1339 (NIR and SWIR). For all three targets, classification accuracies were highest in batch one analysis. As shown in Table 1, single leaf had a classification accuracy should look like of 94.7%, plant canopy, 100%, and plant canopy with soil 100%. In addition, sixteen spectral wavelengths were identified on the MHTK spectral curves. These wavelengths are the best spectral characteristics used in the classification.

TABLE 1

MHTK classification accuracies for reniform nematode population counts in 2001

| Target | Wavelengths Used | Accuracy (%) |
| --- | --- | --- |
| Single | 451–949 | 94.7 |
| Leaf | 451–949, 1001–1339 | 83.3 |
| Plant | 451–949 | 100 |
| Canopy | 451–949, 1001–1339 | 66.7 |
| Canopy + | 451–949 | 100 |
| Soil | 451–949, 1001–1339 | 83.3 |

In addition, sixteen spectral wavelengths were identified on the MHTK spectral curves identified below in Table 2 below as being the best wavelengths for classifying nematode population.

TABLE 2

Wavelengths (nm) for distinguishing *R. reniformis* population levels on cotton using reflectance pooled over the growing season in field microplots, 2001.

| Single leaf | Plant canopy | Canopy and soil |
|---|---|---|
| 451 | 451 | 451 |
| 465 | 472 | 502 |
| 505 | 479 | 523 |
| 602 | 492 | 541 |
| 655 | 502 | 587 |
| 684 | 517 | 620 |
| 782 | 550 | 666 |
| 809 | 591 | 701 |
| 828 | 632 | 723 |
| 850 | 722 | 760 |
| 860 | 768 | 793 |
| 870 | 821 | 828 |
| 883 | 844 | 856 |
| 898 | 883 | 898 |
| 912 | 911 | 923 |
| 944 | 933 | 949 |

EXAMPLE 2

Microplot Study for the 2002 Growing Season

The data collection procedures were followed as performed in the 2001 growing season. Beginning in April 2002, the fields were prepared for research that involved the following: soil nutrient analysis, application of recommended nutrients, planting of cotton, inoculation of microplots with reniform nematodes, sap flow meter preparation. Hyperspectral data collection began the last week of May for both the microplot study and production field study and continued until harvest. The microplots were sampled on the following dates: 28 May, 12 June, 25 June, 09 July, 23 July, 06 August, and 20 August.

Single leaf, plant canopy, and canopy with soil spectral measurements and corresponding reniform nematode population levels were analyzed using the MHTK with SOMs. Water bands and bands containing electronic noise were removed prior to SOM analysis. Two batches of SOMs were run for each target. The first batch concentrated on bands 451–949 (Visible and NIR). The second batch ran with not only wavelengths 451–949, but also 1001–1339 (NIR and SWIR). For single leaf, higher classification accuracy was found using the first batch of bands (491–949) with a classification accuracy of 80% in batch one and 60% in batch two. As shown in Table 2, plant canopy had a classification accuracy of 100% for both batch one and 66.7% for batch two. Canopy with soil classification accuracies were 100% for both batch one and two (Table 2). Sixteen spectral wavelengths were identified on the MHTK spectral curves and were similar to those identified in 2001.

TABLE 3

MHTK classification accuracies for reniform nematode population counts in 2002

| Target | Wavelengths Used | Accuracy (%) |
|---|---|---|
| Single Leaf | 451–949 | 80 |
|  | 451–949, 1001–1339 | 60 |
| Plant Canopy | 451–949 | 100 |
|  | 451–949, 1001–1339 | 66.7 |
| Canopy + Soil | 451–949 | 100 |
|  | 451–949, 1001–1339 | 100 |

The classification accuracies in Table 3 were identified using the 16 wavebands/channels illustrated in Table 4 below:

TABLE 4

Wavelengths (nm) for distinguishing *R. reniformis* population levels on cotton using reflectance pooled by target in field microplots, 2002.

| Single leaf | Plant canopy | Canopy and soil |
|---|---|---|
| 451 | 451 | 451 |
| 470 | 467 | 463 |
| 493 | 504 | 469 |
| 511 | 515 | 480 |
| 560 | 534 | 490 |
| 585 | 582 | 498 |
| 604 | 631 | 509 |
| 654 | 658 | 523 |
| 673 | 729 | 660 |
| 730 | 771 | 717 |
| 799 | 790 | 750 |
| 828 | 822 | 815 |
| 892 | 855 | 856 |
| 911 | 888 | 870 |
| 929 | 898 | 883 |
| 949 | 920 | 927 |

When data from above-described growing seasons and locations was combined and analyzed, the 16 wavebands characterized by the center wavelengths in Table 5 below were determined to be the most useful for characterizing nematode populations for the indicated targets:

TABLE 5

Wavelengths (nm) for distinguishing *R. reniformis* population levels using reflectance data pooled by target over multiple years and locations.

| Single leaf | Plant canopy | Canopy and soil |
|---|---|---|
| 451 | 451 | 451 |
| 472 | 469 | 497 |
| 504 | 487 | 517 |
| 540 | 501 | 542 |
| 620 | 515 | 568 |
| 658 | 546 | 606 |
| 687 | 579 | 640 |
| 730 | 634 | 682 |
| 765 | 678 | 727 |
| 810 | 741 | 761 |
| 844 | 787 | 798 |
| 856 | 812 | 840 |
| 872 | 864 | 862 |
| 906 | 879 | 894 |
| 921 | 838 | 913 |
| 945 | 930 | 948 |

FIG. 3 is a block diagram of a system 300 for detecting the presence and/or extent of nematode infestation according to another embodiment of the invention. The system 300 includes a remote sensor 310. The sensor 310 is preferably capable of collecting reflectance data at the wavelengths set forth in Table 5. In some embodiments, the sensor 310 is a commercially available hyperspectral radiometer; in yet other embodiments, the sensor 310 is a commercially available multispectral radiometer; in yet other embodiments, the sensor 310 is special purpose device built to collect reflectance data at the wavelengths specified above in Table 4. In some embodiments, the sensor 410 is the FIELDSPEC™ PRO spectroradiometer available from Analog Spectral Devices, Inc.

The sensor 310 is connected to a processor 320. The processor 320 is configured to input reflectance data from the sensor 310. In embodiments in which the sensor 310 provides reflectance data at wavelengths beyond the specific wavelengths of interest (e.g., the wavelengths/channels identified in Table 4), the processor 320 filters (e.g., ignores) the reflectance data from wavelengths other than the wavelengths of interest. The system 300 preferably includes an input device 330 by which the user can indicate the type of target (e.g., soil, plant leaf or plant canopy) so that the processor 420 can select the wavelengths of interest (channels) corresponding to the target. However, in other embodiments, the system 300 is directed to a single type of target (e.g., plant canopy) and therefore an input device 330 for selection of target type is not necessary.

In some embodiments, the processor 320 performs a supervised classification using a neural network. In one such embodiment, a back propagation neural network is trained with known nematode reflectance values to create a model for classifying reflectance data from the sensor 310. In some embodiments, the neural network outputs a simple yes/no, indicating whether or not nematode infestation is present. In other embodiments, the neural network outputs an estimate of the nematode population.

In yet other embodiments, a simple thresholding process can be used. In these embodiments, a threshold (which is determined based on reflectance data collected from cotton plants with know nematode populations) is set for each of the wavelengths of interest. The reflectance data for each of the wavelengths of interest from the sensor 310 is compared to the corresponding threshold to determine a yes/no indication for each of the wavelengths of interest. The processor 320 then makes a yes/no determination as to whether nematode infestation is present based on whether the majority of the indications for the individual wavelengths of interest are yes or no. Alternatively, an estimate of the nematode population can be performed by interpolating the reflectance values from each of wavelengths of interest against corresponding reflectance values from cotton plants with known nematode infestations. However, these thresholding techniques are not easily extensible to varying input conditions, such as different types of nematode populations, temporal variances (i.e., time of day and differences in environmental conditions (e.g., sunny vs. cloudy, etc.)), and spatial variances (e.g., differences in spacing between cotton plants). One way in which the system 300 could be extended to deal with such varying input conditions would be to determine thresholds for varying combinations of input conditions and allow the user to provide an indication of the input conditions so that the corresponding thresholds are utilized.

In contrast to the thresholding technique, with the neural network, the results can be generalized to varying input conditions by including data collected under these varying input conditions in the training set for the model.

In some embodiments, the reflectance data from multiple physical locations (e.g., multiple physical locations in a cotton field) are input to a SOM routine prior to being input to the neural network. This serves to reduce the amount of data the neural network must process.

In other embodiments, the output of the neural network (i.e., the classification for each of the data points collected) is input to a SOM routine such that a two dimensional spatial map indicating the spatial distribution of nematode infestation or nematode population levels is created. The resulting self-organized map can be used to determine where and/or how much nematacide (which can be in either liquid or granular form) to apply to the various areas represented by the self-organized map.

The above description serves the purpose of teaching a person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

What is claimed is:

1. A method for detecting nematodes in a target, said method comprising:
    collecting reflectance data at a plurality of wavelengths from said target, each of the wavelengths being a wavelength whose intensity is indicative of a level of nematode infestation; and
    determining the presence of nematodes associated with the target based on the intensities of the reflectance data.

2. The method of claim 1, further comprising the step of analyzing said intensities of said reflectance data to determine nematode population in the target.

3. The method of claim 1, wherein said target is selected from the group consisting of a cotton plant, a cotton plant canopy, a single cotton plant leaf, and soil in a cotton field.

4. The method of claim 1, wherein said reflectance data is collected using a remote sensing device.

5. The method of claim 4, wherein said remote sensing device is an imaging system capable of collecting reflectance data in both the visible and near infrared spectrums.

6. The method of claim 5, wherein said remote sensing device is capable of collecting reflectance data at wavelengths between 450 nanometers and 950 nanometers.

7. The methods of claim 1, wherein the reflectance data is collected using a hyperspectral radiometer.

8. The method of claim 1, wherein the reflectance data is collected using a multispectral radiometer.

9. The method of claim 1, wherein the step determining the presence of nematodes is performed with a MATLAB based hyperspectral tool kit.

10. The method of claim 9, wherein the step of determining the presence of nematodes is performed using a neural network.

11. The method of claim 10, wherein the neural network includes a model trained with reflective data from control groups of cotton plants infested with known nematode populations.

12. A device for detecting or determining the population of reniform nematodes in a target, said device comprising:
    a sensor for collecting reflectance data from said target; and
    a data processor for analyzing intensities of the reflectance data at wavelengths which are associated with the presence of nematodes to determine whether nematodes are present in or at the target.

13. The device of claim 12, wherein said sensor is an imaging system capable of collecting hyperspectral reflectance data at wavelengths between 450 nanometers and 950 nanometers.

14. The device of claim 12, wherein said sensor is an imaging system capable of collecting hyperspectral reflectance data at wavelengths between 450 nanometers and 1340 nanometers.

15. The device of claim 12, wherein said sensor is a hyperspectroradiometer.

16. The device of claim 15, wherein said hyperspectroradiometer is a hand-held hyperspectroradiometer.

17. The device of claim 12, wherein said data processor uses a MATLAB based hyperspectral tool kit.

18. The device of claim 12, wherein the data processor includes a neural network for analyzing intensities of reflectance data.

19. The device of claim 18, wherein the neural network includes a model trained with reflective data from control groups of cotton plants infested with known nematode populations.

20. The device of claim 12, wherein said sensor is an imaging system capable of collecting reflectance data in both the visible and near infrared spectrums.

* * * * *